(12) United States Patent
Stanek et al.

(10) Patent No.: US 8,536,373 B2
(45) Date of Patent: Sep. 17, 2013

(54) METHOD OF PRODUCTION OF 9-CIS-RETINOIC ACID

(75) Inventors: Michael Stanek, Linz (AT); Stefan Essl, Binzen (DE); Monika Knopp, Rheinfelden (CH); Erwin Kübel, Linz (AT)

(73) Assignee: DSM IP Assets B.V., Heerlen (NL)

( * ) Notice: Subject to any disclaimer, the term of this patent is extended or adjusted under 35 U.S.C. 154(b) by 874 days.

(21) Appl. No.: 12/442,162

(22) PCT Filed: Sep. 27, 2007

(86) PCT No.: PCT/EP2007/008399
§ 371 (c)(1),
(2), (4) Date: Feb. 26, 2010

(87) PCT Pub. No.: WO2008/037465
PCT Pub. Date: Apr. 3, 2008

(65) Prior Publication Data
US 2010/0217037 A1   Aug. 26, 2010

(30) Foreign Application Priority Data
Sep. 27, 2006 (AT) ................................ A 1605/2006

(51) Int. Cl.
*C07C 61/00* (2006.01)
(52) U.S. Cl.
USPC ............................ 562/510; 554/124; 554/125

(58) Field of Classification Search
None
See application file for complete search history.

(56) References Cited

U.S. PATENT DOCUMENTS 5,504,230 A * 4/1996 John et al. ................. 554/154
7,015,353 B2 * 3/2006 Soukup et al. ............. 562/510

FOREIGN PATENT DOCUMENTS

EP           0 659 739        6/1995
WO     WO 2004/089887       10/2004

OTHER PUBLICATIONS

International Search Report for PCT/EP2007/008399, mailed Jan. 25, 2008.
Written Opinion of the International Searching Authority for PCT/EP2007/008399, mailed Jan. 25, 2008.

* cited by examiner

*Primary Examiner* — Sudhakar Katakam
(74) *Attorney, Agent, or Firm* — Nixon & Vanderhye P.C.

(57) ABSTRACT

Improved method of production of 9-(Z)-retinoic acid, in which a) a β-formyl-crotonic acid $C_1$-$C_{10}$ alkyl or phenyl ester is reacted with an isolated 9-(Z)—$C_{15}$-triarylphosphonium salt by the Wittig reaction in the presence of a base to the corresponding 9-(Z)-retinoic acid ester; which b) is then saponified with a base to the corresponding 9-(Z)-retinoic acid carboxylate and then, following protonation with an acid, the desired 9-(Z)-retinoic acid is obtained, and improved method for the enrichment and isolation of the 9-(Z)—$C_{15}$-triarylphosphonium salt.

7 Claims, No Drawings

METHOD OF PRODUCTION OF 9-CIS-RETINOIC ACID

This application is the U.S. national phase of International Application No. PCT/EP2007/008399, filed 27 Sep. 2007, which designated the U.S. and claims priority to Austria Application No. A 1605/2006, filed 27 Sep. 2006, the entire contents of each of which are hereby incorporated by reference.

The present invention relates to an improved method of production of 9-cis-retinoic acid.

As is known for example from Nature 355 (1992), pages 359-361, 9-cis-retinoic acid is a physiologically important compound and can be used in a variety of applications, such as for the treatment of various skin diseases (e.g. WO 99/09969).

A method is known from EP 0 659 739 A1 for the production of 9-cis-retinoic acid (9-(Z)-RA) in which a β-formyl-crotonic acid alkyl ester is reacted with a $C_{15}$-triarylphosphonium salt by the Wittig reaction in the presence of a base to the corresponding 9-(Z)-retinoic acid ester, which is then saponified with a base to the desired acid. In this process, the mother liquor that arises in the commercial production of $C_{15}$-triarylphosphonium salts is used as $C_{15}$-triarylphosphonium salt, with the 9-(Z)—$C_{15}$-triarylphosphonium salt fraction being enriched, but not isolated, by treatment with isopropanol while hot, cooling and separation of the crystallizing all-(E)-$C_{15}$-triarylphosphonium salt.

According to WO 2004/089887, a drawback of this method is that it is a two-stage process, in which in addition a change of solvent is necessary for the saponification.

As an improvement, it is proposed to react an alkali-metal salt of 3-methyl-4-oxocrotonic acid with the isolated (Z)-isomer of a $C_{15}$-triarylphosphonium salt in the presence of a base, by which the desired 9-(Z)-retinoic acid is obtained directly.

However, both methods have the disadvantage of low yield of the desired acid. (EP 0 659 739: ~25%; WO 2004/089887: only about 16%).

The task of the present invention was therefore to find an improved method of production of 9-(Z)-retinoic acid, which supplies the desired acid at much higher yields.

Accordingly, the present invention relates to an improved method of production of 9-(Z)-retinoic acid, which is characterized in that a) a β-formyl-crotonic acid-$C_1$-$C_{10}$ alkyl or phenyl ester is reacted with an isolated 9-(Z)—$C_{15}$-triarylphosphonium salt by the Wittig reaction in the presence of a base to the corresponding 9-(Z)-retinoic acid ester, which b) is then saponified with a base to the corresponding 9-(Z)-retinoic acid carboxylate and then, following protonation with an acid, the desired 9-(Z)-retinoic acid is obtained.

According to the present invention, in the first step β-formyl-crotonic acid —$C_1$-$C_{10}$ alkyl or phenyl ester is reacted with an isolated 9-(Z)—$C_{15}$-triarylphosphonium salt by the Wittig reaction in the presence of a base to the corresponding 9-(Z)-retinoic acid ester.

β-Formyl-crotonic acid methyl-$C_1$-$C_{10}$ alkyl or phenyl esters can be prepared for example according to EP 0 421 271.

Alkyl in this case denotes linear, branched or cyclic alkyl residues, such as methyl, ethyl, n-propyl, i-propyl, n-butyl, sec. butyl, tert. butyl, hexyl or cyclohexyl.

Preferably the β-formyl-crotonic acid methyl or ethyl ester is used as educt.

9-(Z)—$C_{15}$-Triarylphosphonium salts are compounds of formula (I)

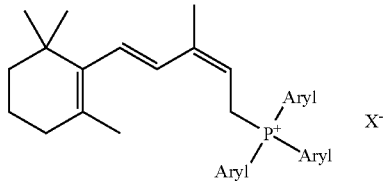

in which aryl represents an optionally substituted $C_6$-$C_{10}$-aryl residue, such as phenyl, naphthyl, tolyl or xylyl and X represents a halogen, such as chlorine, bromine or iodine. Preferably aryl denotes a phenyl residue and X denotes chlorine or bromine.

According to the present invention, the 9-(Z)—$C_{15}$-triarylphosphonium salt is used in isolated form.

A mother liquor that arises in the industrial production of $C_{15}$-triarylphosphonium salts is used for this. Thus, for example in the production of the $C_{15}$-triarylphosphonium salt required for industrial vitamin-A syntheses, β-carotene syntheses and canthaxanthin syntheses, and for the production of other vitamin-A derivatives, such as retinal and retinoic acid, (see e.g. Angew. Chem. 77 (1965), 277-360) after separating the valuable product a mother liquor is obtained that contains the 9-(Z) isomer as well as all-(E)-$C_{15}$-triphenylphosphonium salt.

For the method according to the invention the 9-(Z) isomer is first enriched, and then isolated.

For this, preferably a) the mother liquor is extracted with methylene chloride, then
b) the organic phase is re-extracted with water and
c) the methylene chloride phase is separated from the aqueous phase, then
d) 50-70% methylene chloride is distilled off, and
e) ethyl acetate and seed crystals are added to the concentrated methylene chloride solution at 15-40° C., preferably at 20-30° C., then
f) the solution is stirred at 15-40° C., preferably at 20-30° C., and the enriched 9-(Z) isomer precipitates and
g) then the enriched 9-(Z)—$C_{15}$-triarylphosphonium salt is separated by filtration while moist, and is washed with ethyl acetate.
h) Next, the 9-(Z) isomer is dissolved in methylene chloride and this solution is added dropwise at 20-40° C., preferably at 15-30° C., to a defined amount of ethyl acetate, then
i) the resultant suspension is stirred and
j) finally the enriched 9-(Z)—$C_{15}$-triarylphosphonium salt is separated by filtration, washed with ethyl acetate and then dried.

With this method of enrichment, which is improved relative to the state of the art, an isolated 9-(Z)—$C_{15}$-triarylphosphonium salt is obtained with a ratio of Z fraction to E fraction of 98:2.

If necessary, steps h-j can be omitted, obtaining a higher yield of 9-(Z)—$C_{15}$-triarylphosphonium salt, but of somewhat lower purity (with a ratio of Z fraction to E fraction of 96:4). This quality is, however, also sufficient for production of 9-(Z)—retinoic acid according to the invention.

This improved method of enrichment is also an object of the present invention.

The Wittig reaction of the β-formyl-crotonic acid ester ($C_5$— ester) with the isolated 9-(Z)—$C_{15}$-triarylphosphonium salt is then carried out in a solvent mixture of a $C_1$-$C_4$ alcohol, such as methanol, ethanol, etc. and a non-polar solvent from the group methylene chloride, hexane or toluene.

A dichloromethane-alcohol mixture is preferably used.

The molar ratio of $C_{15}$ salt to $C_5$ ester is 1:1 to 1:5, preferably 1:1 to 1:2, especially preferably 1:1.1.

The reaction temperatures are from −40 to +40° C., preferably from −30 to −20° C., depending on the composition of the solvent mixture.

The base used in the method according to the invention is an alkali-metal or alkaline-earth $C_1$-$C_4$ alcoholate, carbonate, hydroxide, hydride or amide. Li-, Na- or K-alcoholates, carbonates, hydroxides, hydrides and amides are preferred, and sodium methylate, ethylate or propylate, sodium hydroxide and potassium carbonate are especially preferred.

It is possible to start either with both starting compounds in the solvent mixture, then adding the base, or it is also possible to add one of the educts, either the $C_{15}$ salt or the β-formyl-crotonic acid ester.

Preferably only the base is added.

The Wittig reaction leads to the retinoic acid ester. Isolation takes place after separation of the non-polar solvent, replacing it with a protic, polar solvent, so that the volume remains constant at normal pressure. Preferably dichloromethane is distilled off and methanol is fed in, maintaining constant volume. Then hexane, cyclohexane, heptane, toluene or some other suitable solvent (depending on the ester substituent) is added to the remaining protic, polar solvent and the retinoic acid ester is extracted into the non-polar phase.

However, isolation of the retinoic acid alkyl ester can be omitted. At the end of the Wittig reaction the mixture is heated to room temperature and saponified with an aqueous alkali-metal or alkaline-earth hydroxide solution. For this, the reaction mixture is heated further to 30 to 100° C., preferably to 50-80° C. and all low-boiling substances are distilled off. Then by adding an acid, such as HCl, $H_2SO_4$, acetic acid, phosphoric acid, etc., to the cooled alkaline reaction mixture, the 9-(Z)-retinoic acid is released and crystallizes out.

The 9-(Z)-retinoic acid thus obtained can then be purified by extraction, optionally in combination with recrystallization. The preferred solvents for extraction are water and dichloromethane. Recrystallization is preferably carried out in $C_1$-$C_4$ alcohols or $C_1$-$C_4$ alcohol mixtures, preferably ethanol.

Using the method according to the invention, 9-(Z)-retinoic acid is obtained at much higher yields compared with the state of the art, of more than 45% of the theoretical, and also at higher purities of >98%.

EXAMPLE 1

Enrichment of the $C_{15}$ Salt According to the Invention 300 g of mother liquor (containing approx. 30% of valuable product) from the production of $C_{15}$-triphenylphosphonium chloride was mixed with 240 ml dichloromethane and stirred for 30 min. Then the phases were separated and the organic phase was washed with 450 ml water. 5 g of table salt was added to the aqueous phase. The phases were separated and the aqueous phase was extracted again with 150 ml dichloromethane. The combined organic phases were concentrated at 40° C. Approx. 240 ml dichloromethane was distilled off, so that 150 ml dichloromethane remained in the flask. The mixture was cooled to 25° C., 1500 ml ethyl acetate and a spatula tip of seed crystals were added, and filtration was carried out after 60 min. The precipitate was washed with 150 ml ethyl acetate.

Recrystallization:

The raw product was dissolved in 150 ml dichloromethane and then added in the space of 30 min at 30° C. to 1500 ml ethyl acetate while stirring. After stirring for a further 30 min, the 9-(Z)—$C_{15}$-triphenylphosphonium chloride was filtered off and washed twice with 150 ml ethyl acetate each time, and dried to constant weight. 9-(Z)—$C_{15}$-Triphenylphosphonium chloride was obtained at a yield of 69 g and a purity of >97% (Z). The yield was 66.9%

EXAMPLE 2

Production of 9-(Z)-retinoic Acid a) Wittig Reaction:

First, a double-jacket reactor was gassed with nitrogen for at least 15 min.

Then 51.13 g $C_{15}$-vinyl salt (content of cis+trans C15 vinyl salt >98.5%) and 14.24 g $C_5$ ester (w=0.99) were added with a disposable syringe. Residues of substance in the funnel were rinsed with 276.85 g (350 ml) methanol (w=1.0) into the reactor and the slightly yellowish solution was cooled under a gentle stream of nitrogen to an internal temperature of −7.5° C.

Then 50.42 g (52.0 ml) sodium methylate was fed in at −7.5° C. internal temperature in the space of 60 minutes.

Then 157.80 g (200.0 ml) of ethanol (w=1.0) was added.

b) Saponification/Hydrolysis 48.52 g (37.14 ml) NaOH (28%) was fed in at 20° C. and the orange suspension was heated to reflux. After distillation of methanol/ethanol the suspension was cooled to room temperature and 265.00 g (200 ml) methylene chloride, 299.40 g (300 ml) water and 71.00 g (67.7 ml) acetic acid were added.

c) Extraction 662.5 g (500 ml) methylene chloride was added to the above solution and the organic phase was extracted twice, each time with 199.6 g (200 ml) water WBI (w=1.0).

Then the combined organic phases were concentrated in the rotary evaporator at 35° C., obtaining raw retinoic acid.

d) Recrystallization

The raw retinoic acid thus obtained was suspended in 235.5 g (300 ml) isopropanol (w=1.0) and refluxed.

Then it was crystallized and the crystals were filtered off. The crystals were washed with approx. 39.55 g (50 ml) isopropanol −10° C. (w=1.0) and then dried at high vacuum.

Yields

| Products | Quantity [g] | Content (cis-RTA) [%] | Quantity 100% [g] | Molar mass [g/mol] | Yield (trans) based on C-15 vinyl salt used [% of theor.] |
|---|---|---|---|---|---|
| Retinoic acid | Approx. 14 g | Approx. 98 | 13.7 | 300.44 | Approx. 46 |

EXAMPLE 3

Comparative Test According to BASF Patent

The yields stated in the BASF patent (EP0659739) were verified in the laboratory (Table).

EXAMPLE 4

Comparative Test According to Roche Patent

The yields stated in the Roche patent (WO2004/089887) were verified in the laboratory (Table).

|  | BASF | Roche | DSM |
|---|---|---|---|
| Yield Vinyl salt | 46% | 31% | 67% |
| Content: | 65.8% Z | 93.6% Z | 98% Z |
|  | 19.0% E | 5% E | 2% E |
| Yield Retinoic acid incl. recrystallization | 25% | 15.5% | 40-45% |
| Content: | 99.5% | ??% | >99.5% |

The invention claimed is:

1. A method for producing 9-(Z)-retinoic acid, comprising:
  a) reacting a β-formyl-crotonic acid —$C_1$-$C_{10}$ alkyl or phenyl ester with an isolated 9-(Z)—$C_{15}$-triarylphosphonium salt by a Wittig reaction in the presence of a base to form a reaction mixture comprising a corresponding 9-(Z)-retinoic acid ester,
  b) saponifying the 9-(Z)-retinoic acid ester with a base to form the corresponding 9-(Z)-retinoic acid carboxylate, and then
  c) protonating the 9-(Z)-retinoic acid carboxylate with an acid to obtain 9-(Z)-retinoic acid.

2. The method according to claim 1, wherein the isolated 9-(Z)—$C_{15}$-triarylphosphonium salt is a compound of formula (I)

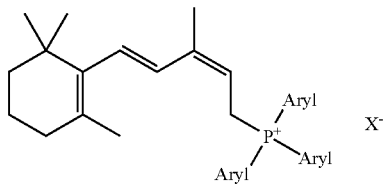

in which Aryl represents an optionally substituted $C_6$-$C_{10}$ aryl residue and X represents a halogen.

3. The method according to claim 1, wherein the reaction in step a) takes place in a solvent mixture of a $C_1$-$C_4$ alcohol and a non-polar solvent selected from the group consisting of methylene chloride, hexane and toluene.

4. The method according to claim 1, wherein the reaction in step a) is carried out at a reaction temperature from −40° C. to +40° C.

5. The method according to claim 1, wherein the reaction in step a) takes place in the presence of a base selected from the group consisting of the alkali-metal or alkaline-earth $C_1$-$C_4$ alcoholates, carbonates, hydroxides, hydrides and amides.

6. The method according to claim 1, wherein the 9-(Z)-retinoic acid ester obtained according to step a) is not isolated from the reaction mixture, and wherein step a) comprises after the end of the Wittig reaction the steps of optionally heating the reaction mixture is to room temperature, and wherein step b) includes saponifying the 9-(Z)-retinoic acid ester with an aqueous alkali-metal or alkaline-earth hydroxide solution as base.

7. The method according to claim 1, wherein step b) sequentially comprises (b1) adding the base to form an alkaline reaction mixture, b2) distilling off the low-boiling substances, b3) cooling the alkaline reaction mixture and then, b3) adding an acid to the cooled alkaline reaction mixture to thereby release and crystallize the desired 9-(Z)-retinoic acid.

* * * * *